(12) United States Patent
Hsieh

(10) Patent No.: US 9,839,556 B2
(45) Date of Patent: Dec. 12, 2017

(54) HEAT AND LOW-FREQUENCY TREATMENT DEVICE

(71) Applicant: NITTO TECHNOLOGY INC., Taichung (TW)

(72) Inventor: Chu Yu Hsieh, Taichung (TW)

(73) Assignee: Nitto Technology Inc., Taichung (TW)

( * ) Notice: Subject to any disclaimer, the term of this patent is extended or adjusted under 35 U.S.C. 154(b) by 127 days.

(21) Appl. No.: 15/079,993

(22) Filed: Mar. 24, 2016

(65) Prior Publication Data

US 2017/0273822 A1 Sep. 28, 2017

(51) Int. Cl.
*A61N 1/04* (2006.01)
*A61F 7/00* (2006.01)
*A61N 1/20* (2006.01)

(52) U.S. Cl.
CPC ............ *A61F 7/007* (2013.01); *A61N 1/0492* (2013.01); *A61N 1/205* (2013.01); *A61F 2007/0094* (2013.01)

(58) Field of Classification Search
None
See application file for complete search history.

(56) References Cited

FOREIGN PATENT DOCUMENTS

| JP | 4755916 B2 | 8/2011 |
|---|---|---|
| JP | 5148254 B2 | 2/2013 |

*Primary Examiner* — Ankit D Tejani
(74) *Attorney, Agent, or Firm* — Muncy, Geissler, Olds & Lowe, P.C.

(57) ABSTRACT

The disclosure relates to a heat and low-frequency treatment device, which includes a host, a control circuit and two cushions. The control circuit has an input interface, a processor, an amplifying circuit and a negative half-wave elimination circuit. When the two cushions receive the power controlled by the processor, according to control waveform and voltage the current is flowed through the treatment site where it is covered by the two cushions, and the heat energy generated by the electric heating layer is transmitted to the deep of the treatment site at the same time.

6 Claims, 12 Drawing Sheets

HEAT AND LOW-FREQUENCY TREATMENT DEVICE

BACKGROUND OF THE INVENTION

1. Field of the Invention

The present disclosure relates to a heat and low-frequency treatment device, and more particularly to the treatment device capable of transmitting heat energy to the deep of treatment sites of a body along with the current.

2. Description of the Related Art

As shown in FIG. 12, a conventional massager has a host 91 and two electrode pieces 92 connected with the host 91 by wires 93. While the massager is used, the two electrode pieces 92 are pasted to the body's site to be massaged. After the massage mode is set, the host 91 can start to output the low-frequency current to the electrode pieces 92, to perform a discharging treatment (that is, the positive electrode and the negative electrode are conducted on the same electrode piece 92) to irritate the surface skin or the shallow muscle by the electrode pieces 92. Thus, the user may feel limp and numb on the skin pasted with the electrode pieces 92, and the user's muscle may generate an unconscious contraction, so as to achieve the effect of relaxing muscle by massaging.

However, although the low-frequency current generated by the host 91 and discharged through the electrode pieces 92 may achieve the aforesaid massage relaxing effect, the irritation effect is just generated on the surface skin or the shallow muscle only, and may not be transmitted to the deep muscle of the body. In addition, the reaction generated by discharging to the skin and the muscle may bring about several side effects, such as the skin illness and the muscle over-contraction.

According to Japanese Patent No. 4,755,916 and No. 5,148,254, it is to be understood that the disclosed electrotherapy devices may include a heating layer for the electrotherapy treatment. The range of the voltage for the supplying power is between 0.3 volts and 20 volts. In other words, the conductive current is small. As a result, the heat energy is just transmitted to the shallow layer of the body but not the deep treatment of the body.

SUMMARY OF THE INVENTION

The objective of the present disclosure is to provide a heat and low-frequency treatment device to solve the aforementioned problems. The device may transmit the heat to the deep of the body along with the current, so as to improve the blood circulation of the treatment site. Besides, the control signal is processed by the negative half-wave elimination circuit to eliminate the negative half wave, so that the user may not be irritated by the negative half cycle wave during the discharging treatment, and the illness in the treatment process can be prevented.

To realize the objective described as above, the present disclosure includes a host, a control circuit and two cushions.

The host has a DC power supply.

The control circuit is disposed on the host and electrically connected to the DC power supply, and includes an input interface, a processor, an amplifying circuit and a negative half-wave elimination circuit. The input interface has a switch and an encoder. The processor provides a control signal according to an operation on the input interface. The DC power supply is electrically connected with two output electrodes through the negative half-wave elimination circuit and the amplifying circuit. One of the two output electrodes is a positive electrode and the other is a negative electrode. When the two output electrodes are conducted to each other, the voltage between the two output electrodes are in a range from 30 to 80 volts with a frequency from 50 to 60 hertz, correspondingly, and a conductive current can be adjusted by an user to be less than or equal to 80 mA. The negative half-wave elimination circuit is connected to the processor and the amplifying circuit correspondingly, and configured to receive the control signal and generate a positive half cycle wave with a peak time of about 0.2 millisecond according to the control signal, and use a diode to eliminate a negative half cycle wave generated by the DC power supply. A control wave can be continuously generated according to the above cycle while the DC power supply supplies the power.

The two cushions are disposed on opposite sides of a treatment site of a body. Each of the two cushions has an electrode layer configured to be pasted to the treatment site and an electric heating layer configured to cover the electrode layer. The electric heating layer is electrically connected with the processor for power control. Each of the electrode layer is made of conductive materials. The electrode layers of the two cushions are electrically connected to the two output electrodes correspondingly. When the processor controls the DC power supply to supply the power, the current according to the aforesaid control wave and the voltage is passed through the treatment site from the cushion connected with the positive electrode to the cushion connected with the negative electrode, and the heat energy generated by the electric heating layer is transmitted to the deep of the treatment site.

Preferably, the negative half-wave elimination circuit has an optical coupler with an open circuit detection function. The optical coupler comprises a detection circuit and a light emitting diode. The light emitting diode produces light while being conducted by the DC power supply. The detection circuit generates no signal while the light emitting diode produces light, and transmits a feedback signal to the processor while the light emitting diode does not produce light, so as to reset the voltage to a minimum value for the user's another setting.

Preferably, the negative half-wave elimination circuit is connected to a half bridge circuit to be a switch of outputting the current.

Preferably, the host has a monitor configured to display the operating information and a buzzer configured to generate warning sound.

Preferably, the input interface may be a remote controller.

BRIEF DESCRIPTION OF THE DRAWINGS

The detailed structure, operating principle and effects of the present disclosure will now be described in more details hereinafter with reference to the accompanying drawings that show various embodiments of the present disclosure as follows.

DETAILED DESCRIPTION OF THE PREFERRED EMBODIMENTS

Please refer to FIG. 1 to FIG. 11, which illustrate a structure according to the embodiment of the present disclosure. It is to be understood that the description is illustrative of exemplary embodiments and is not to be construed as limited to the specific embodiments disclosed.

Figure 1:
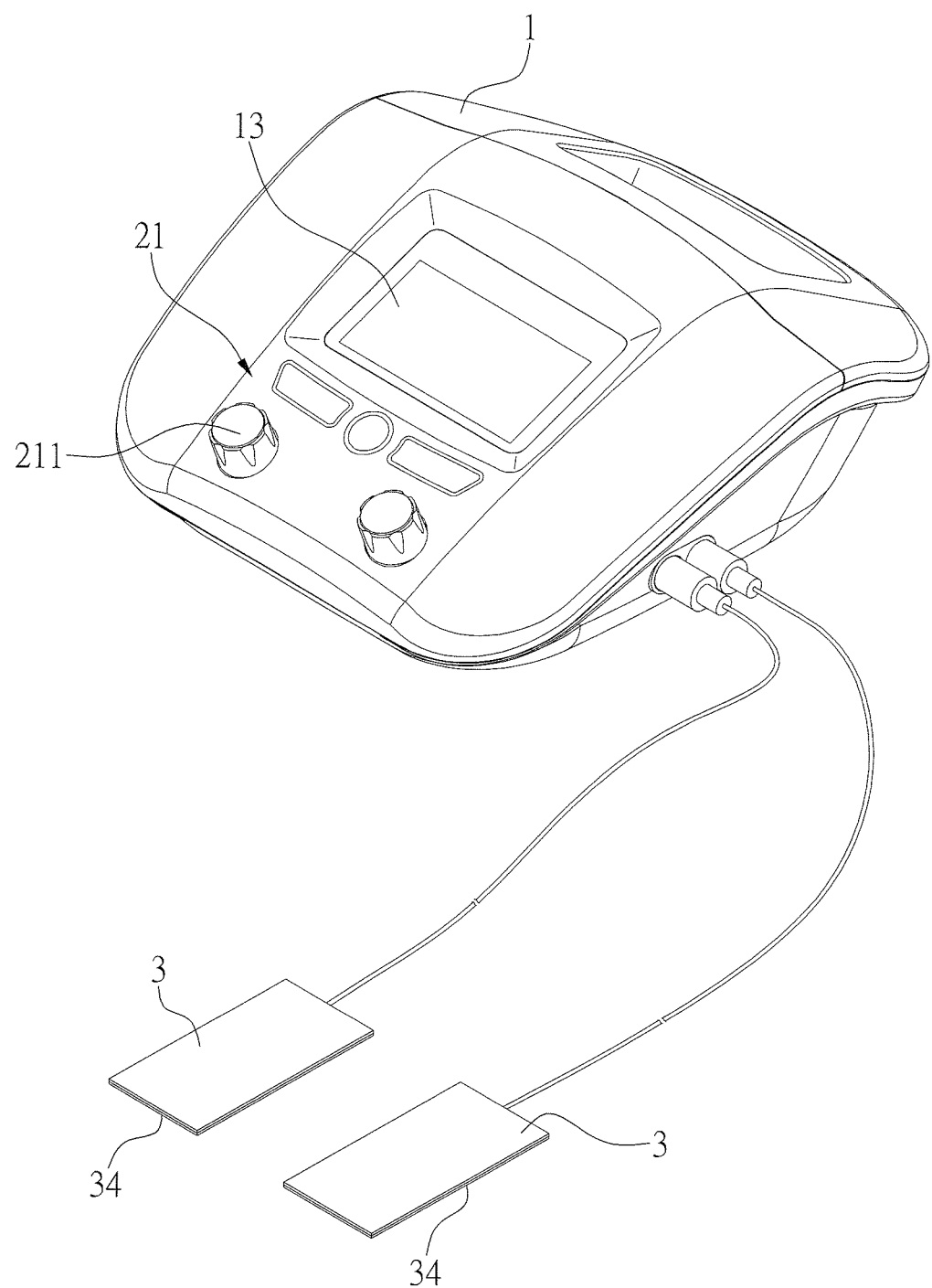
FIG. 1 illustrates a schematic diagram of the treatment device of the present disclosure.
Figure 2:
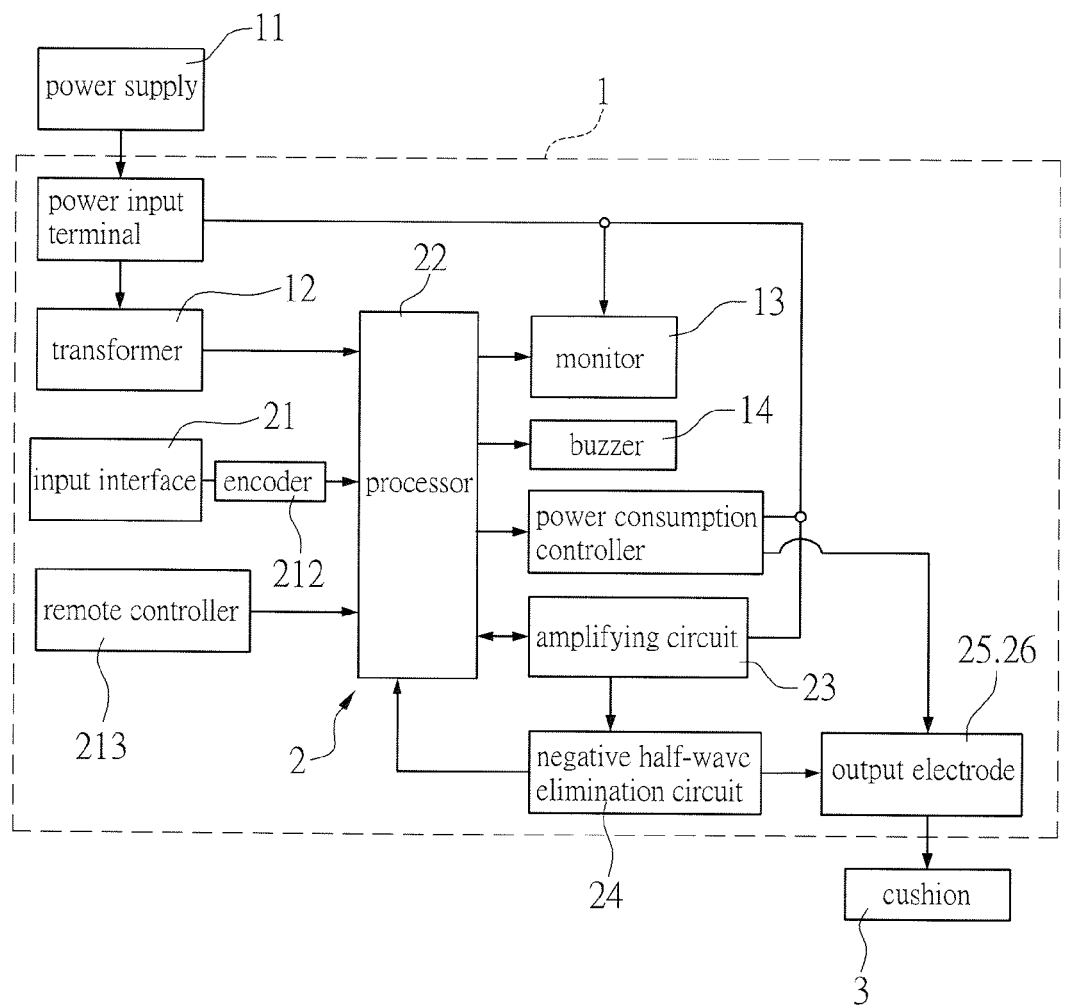
FIG. 2 illustrates a block diagram of the internal circuit configuration of the host of the present disclosure.
Figure 3:
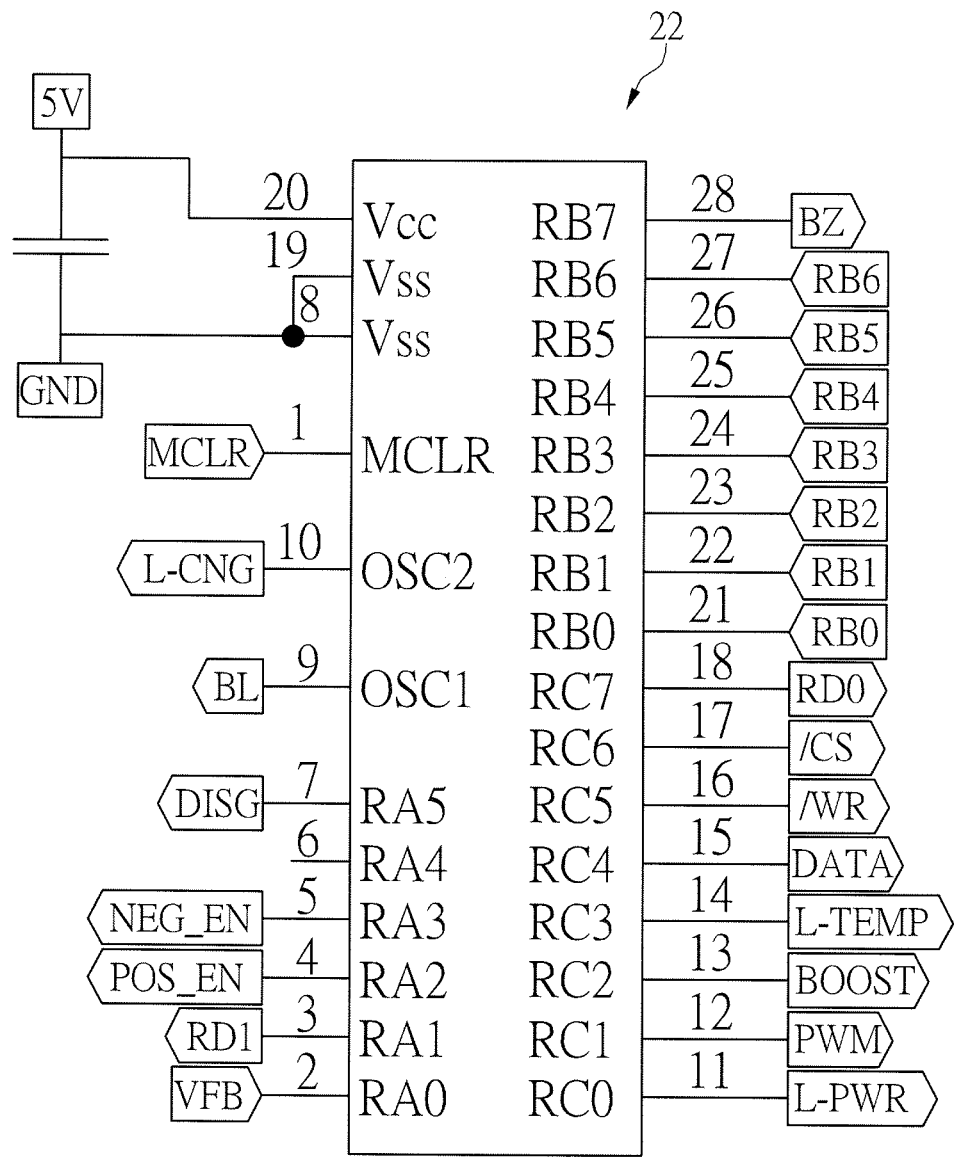
FIG. 3 illustrates a circuit diagram of the processor of the present disclosure.
Figure 4:
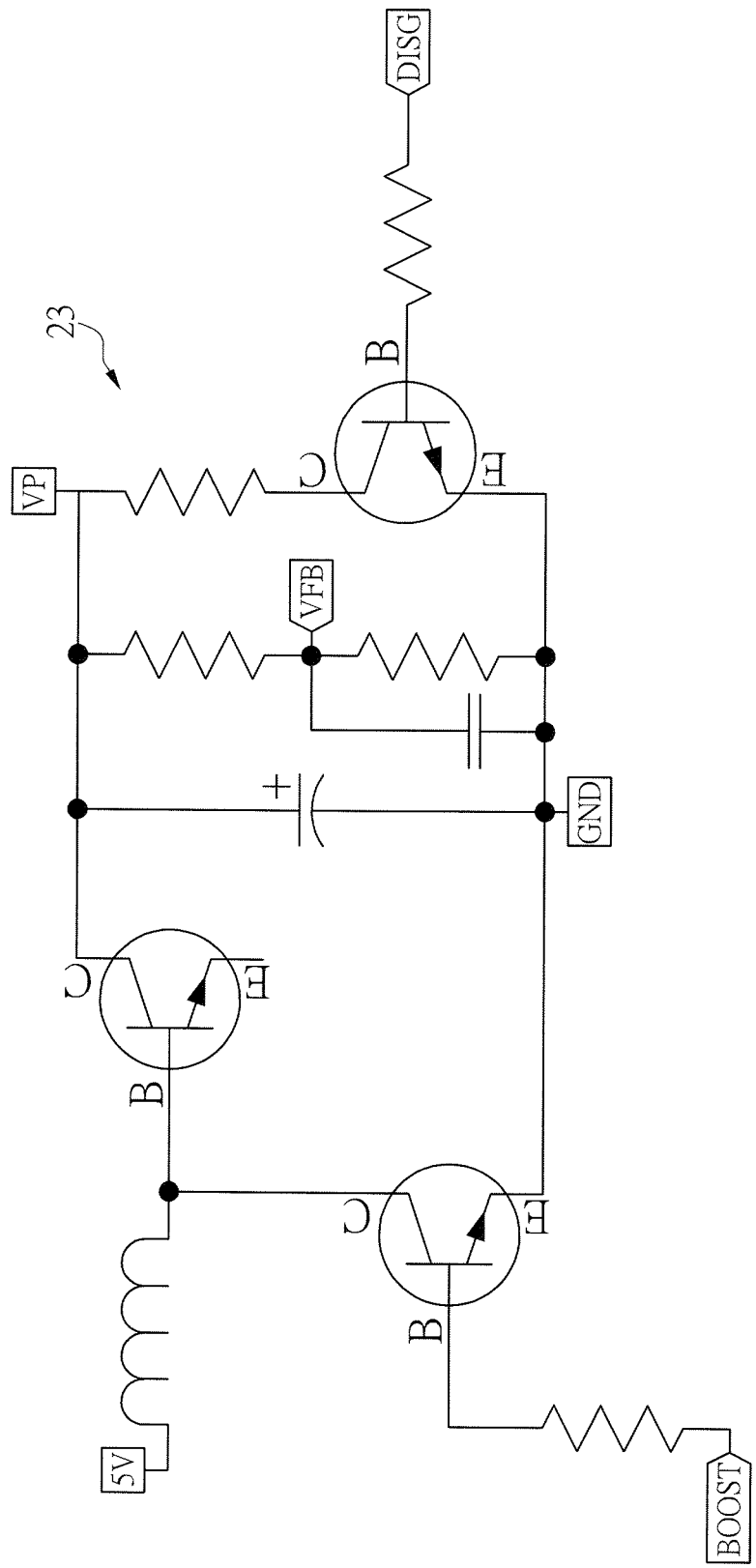
FIG. 4 illustrates a circuit diagram of the amplifying circuit of the present disclosure.

The present embodiment provides a heat and low-frequency treatment device, as illustrated in FIG. 1 and FIG. 2. The treatment device has a host 1, a control circuit 2 and two cushions 3.

As shown in FIG. 2, the host 1 includes a DC power supply. In accordance with the present embodiment, the DC power supply is a direct current power supply with 12 volts/3 amperes provided by a power supply 11. A transformer 12 transforms the DC power supply with 12 volts to the DC power supply with 5 volts, so as to supply the power to the control circuit 2 for operation. As illustrated in FIG. 1 and FIG. 2, in accordance with the present embodiment, the host 1 has a monitor 13 and a buzzer 14. The monitor 13 is configured to display operating information during the treatment and the buzzer 14 is configured to generate warning sound when there is an abnormal situation.

As shown in FIG. 2, the control circuit 2 is disposed on the host 1 and electrically connected to the DC power supply. As illustrated in FIGS. 2 to 5, the control circuit 2 has an input interface 21, a processor 22, an amplifying circuit 23 and a negative half-wave elimination circuit 24. The input interface 21 includes a switch 211 and an encoder 212. The processor 22 provides a control signal according to the operation on the input interface 21. Besides, the input interface 21 may include a remote controller 213.

Figure 5:
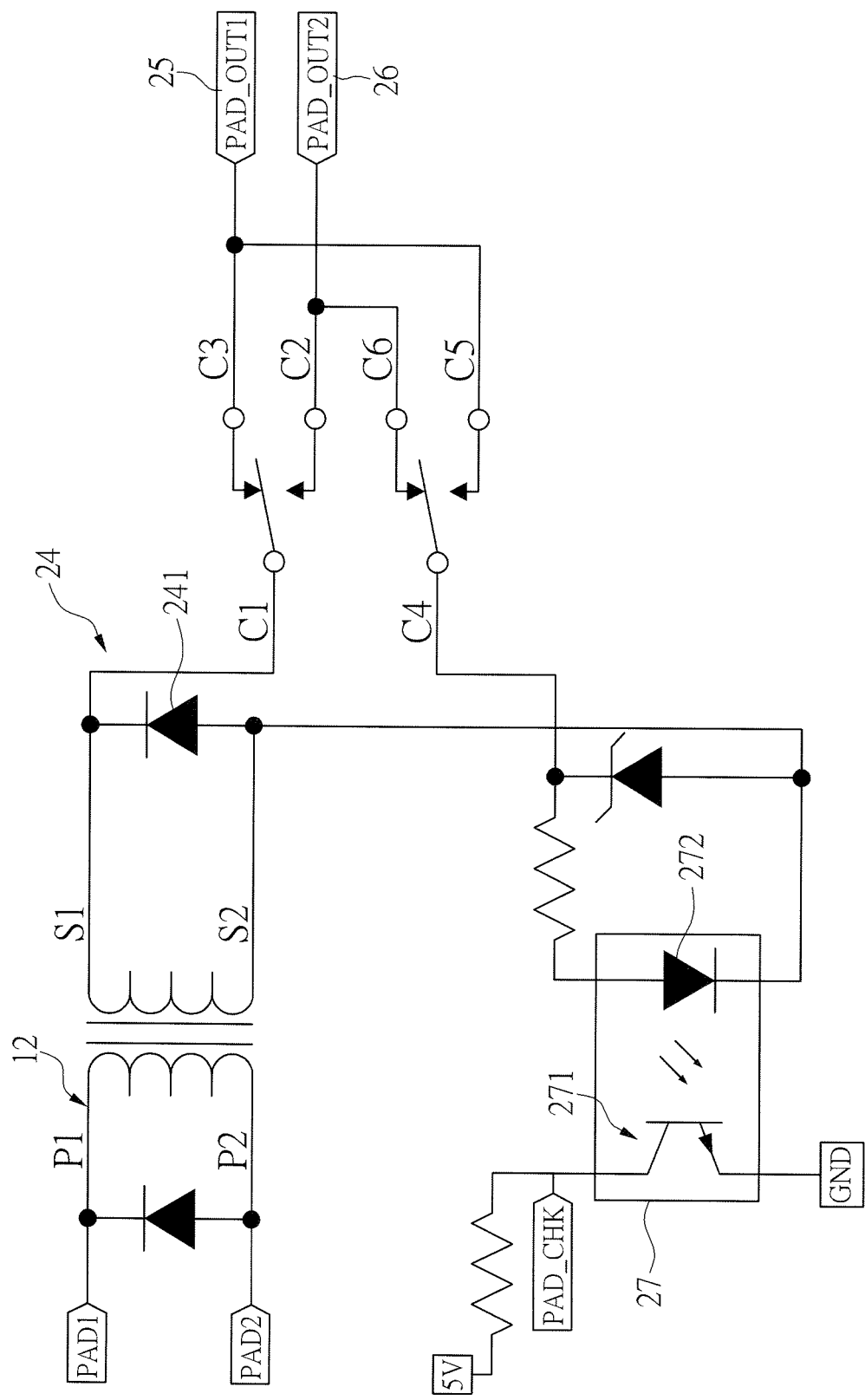
FIG. 5 illustrates a circuit diagram of the negative half-wave elimination circuit of the present disclosure.

As shown in FIG. 5, the aforesaid DC power supply is electrically connected with two output electrodes 25 and 26 through the negative half-wave elimination circuit 24 and the amplifying circuit 23. One of the two output electrodes 25 and 26 is a positive electrode and the other is a negative electrode. In the embodiment, the output electrode 25 is the positive electrode and the output electrode 26 is the negative electrode. When the two output electrodes 25 and 26 are conducted to each other, the voltage between the two output electrodes may be in a range from 30 to 80 volts with a frequency from 50 to 60 hertz, and a conductive current can be adjusted by the user to be less than or equal to 80 mA, where the aforesaid current may be dependent on the resist of the body. The negative half-wave elimination circuit 24 is connected to the processor 22 and the amplifying circuit 23 correspondingly, and configured to receive the control signal and generate a positive half cycle wave with a peak time of about 0.2 millisecond according to the control signal, and then use a diode 241 to eliminate a negative half cycle wave generated by the DC power supply. Therefore, a control wave can be continuously generated according to the above cycle while the DC power supply supplies the power.

Figure 6:
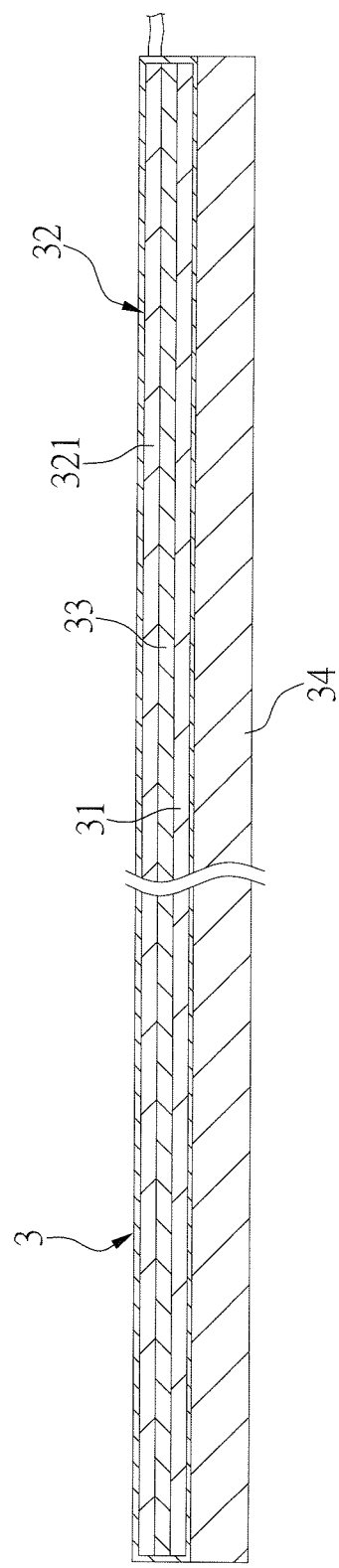
FIG. 6 illustrates a schematic diagram of an internal structure of the cushion of the present disclosure.

As shown in FIG. 6, the two cushions 3 are disposed on opposite sides of a treatment site of a body. Each of the two cushions 3 has an electrode layer 31 configured to be pasted to the treatment site and an electric heating layer 31 configured to cover the electrode layer 32. The electric heating layer 32 is electrically connected with the processor 22 for power control. Each of the electrode layers 31 is made of conductive materials. The electrode layers 31 of the two cushions 3 are electrically connected to the two output electrodes 25 correspondingly. When the processor 22 controls the DC power supply to supply the power, the current according to the aforesaid control wave and the voltage is flowed through the treatment site from the cushion 3 connected with the positive electrode to the cushion 3 connected with the negative electrode, and the heat energy generated by the electric heating layer 32 is transmitted to the deep of the treatment site. In the present embodiment, there is a compartment layer 33 between the electrode layer 31 and the electric heating layer 32 of each of the two cushions 3. A soft layer 34 is disposed on the side of the cushion 3 facing the electrode layer 31. When the cushion 3 is pasted to the treatment site, the soft layer 34 may be in contact with the body.

Figure 7:
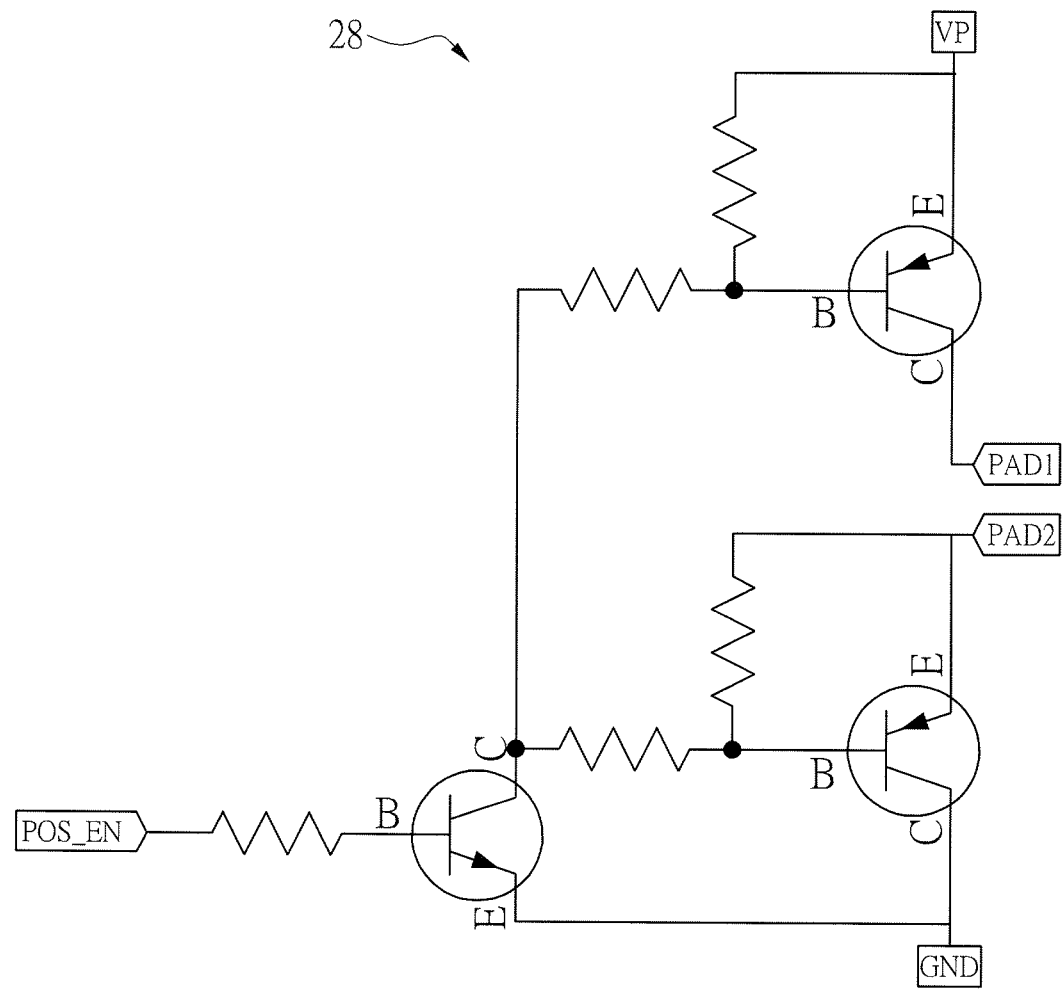
FIG. 7 illustrates a circuit diagram of the half bridge circuit of the present disclosure.

As shown in FIG. 5, the negative half-wave elimination circuit 24 includes an optical coupler 27 with an open-circuit detection function in the present embodiment. The optical coupler 27 is composed of a detection circuit 271 and a light emitting diode 272. The light emitting diode 272 produces light while being conducted with the DC power supply. The detection circuit 271 generates no signal while the light emitting diode 272 produces light, and the detection circuit 271 may transmit a feedback signal to the processor 22 while the light emitting diode 272 does not produce light, so as to reset the voltage to a minimum value for the user's another setting. Further, as shown in FIG. 7, the negative half-wave elimination circuit 24 is connected to a half bridge circuit 28 to be a switch of outputting the current. In the present embodiment, the DC power supply supplies a power of 5 volts for the generation of the feedback signal.

Figure 8:
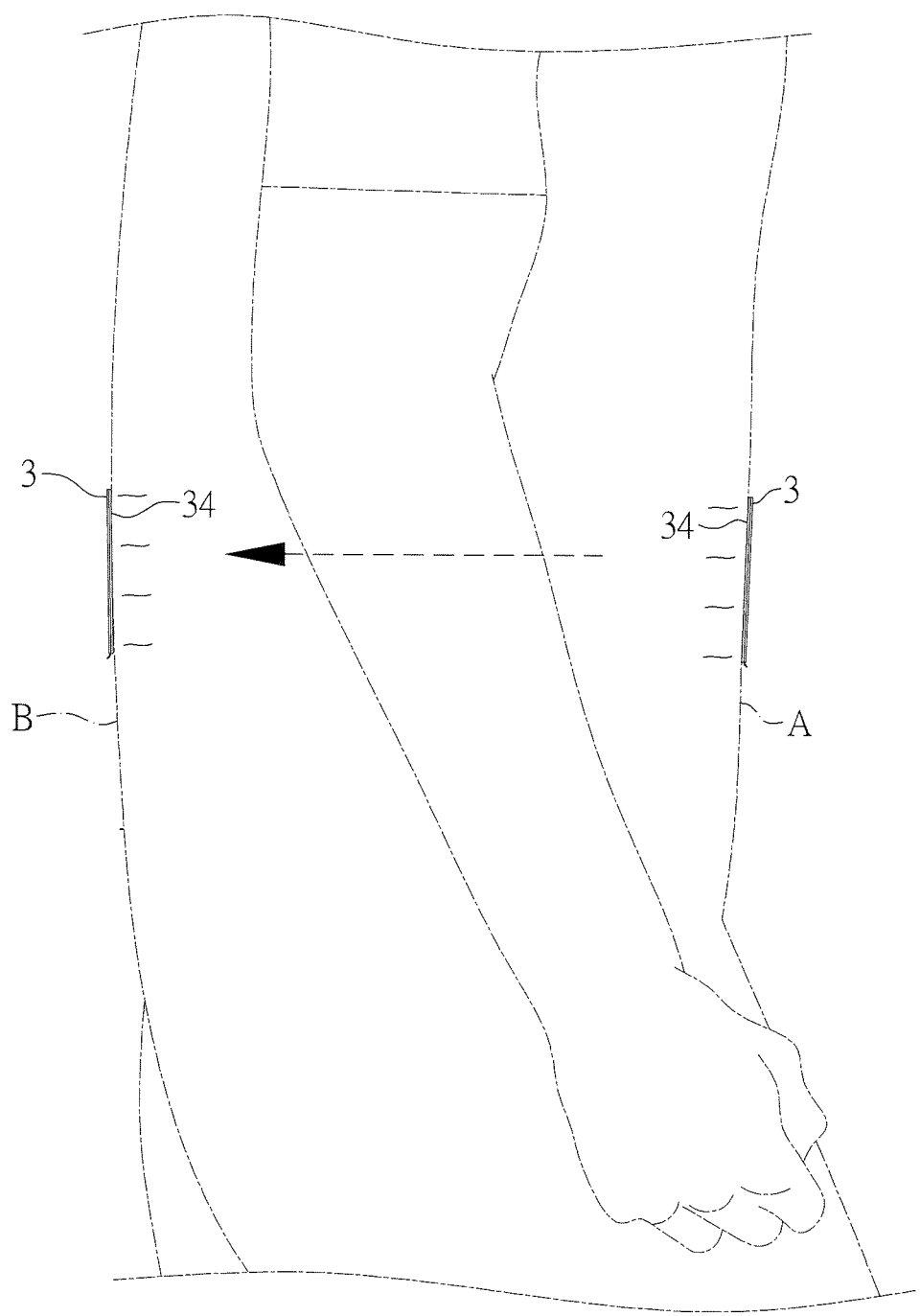
FIG. 8 illustrates a schematic diagram of using the treatment device between the abdomen and back of the body of the present disclosure.

The above heat and low-frequency treatment device may be used for a treatment site of four limbs or body. As shown in FIG. 8, a cushion 3 electrically connected with the output electrode 25 of the positive electrode is pasted to the abdomen A, and the other cushion 3 electrically connected with the output electrode 26 of the negative electrode is pasted to the back B, where these two cushions 3 have the same heights. Next, the host 1 is powered on by operating the switch of the input interface 21. The aforesaid voltage of 30 to 80 volts with the frequency of 50 to 60 hertz is generated by the operations of the processor 22, the amplifying circuit 23 and the negative half-wave elimination circuit 24 of the control circuit 2, where the current is 80 mA. The current is passed through the body from the electrode layer 31 of the cushion 3 of the abdomen A to the electrode layer 31 of the cushion 3 of the back B. The heat energy generated by the electric heating layer 32 may penetrate through the abdomen A and the back B along with the current, so as to transmit the heat energy to the deep muscle of the abdomen.

Figure 9:
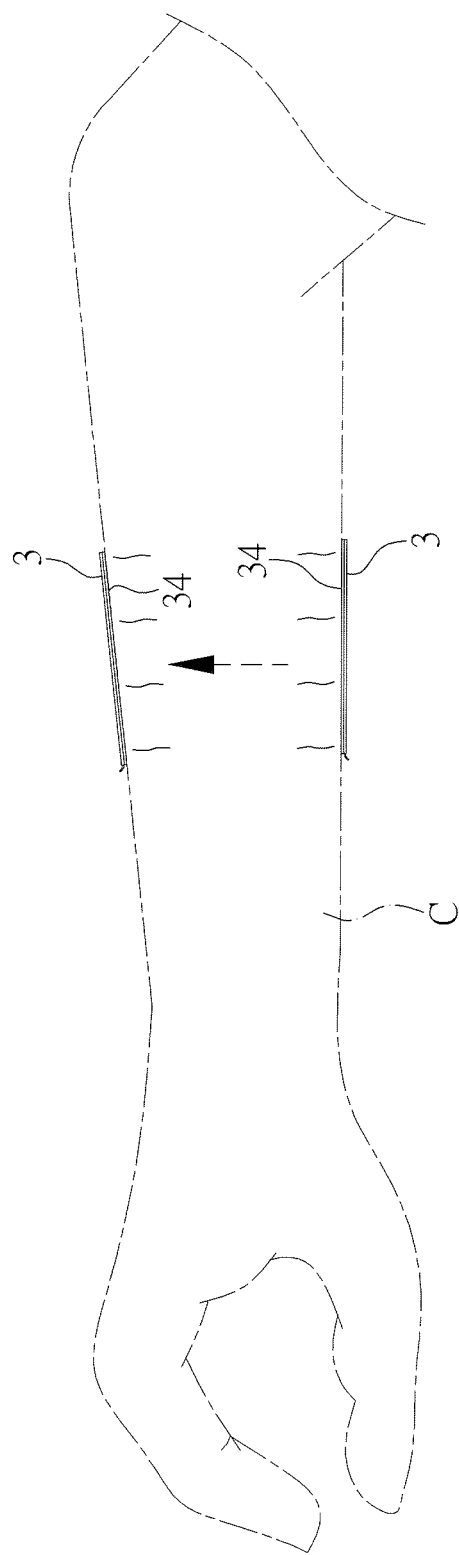
FIG. 9 illustrates a schematic diagram of using the treatment device between the upper and the bottom surface of an arm of the body of the present disclosure.

As shown in FIG. 9, the arm C is the aforesaid treatment site to be chosen. A cushion 3 electrically connected with the output electrode 25 of the positive electrode is pasted to the bottom surface of the arm, and the other cushion 3 electrically connected with the output electrode 26 of the negative electrode is pasted to the upper surface of the arm C. Like the aforesaid operation of pasting the cushions 3 to the abdomen A and the back B, the heat energy generated by the electric heating layer 32 may penetrate through the upper arm C and the bottom arm C along with the current in the same way, so as to transmit the heat energy to the deep muscle of the arm C.

Figure 10:
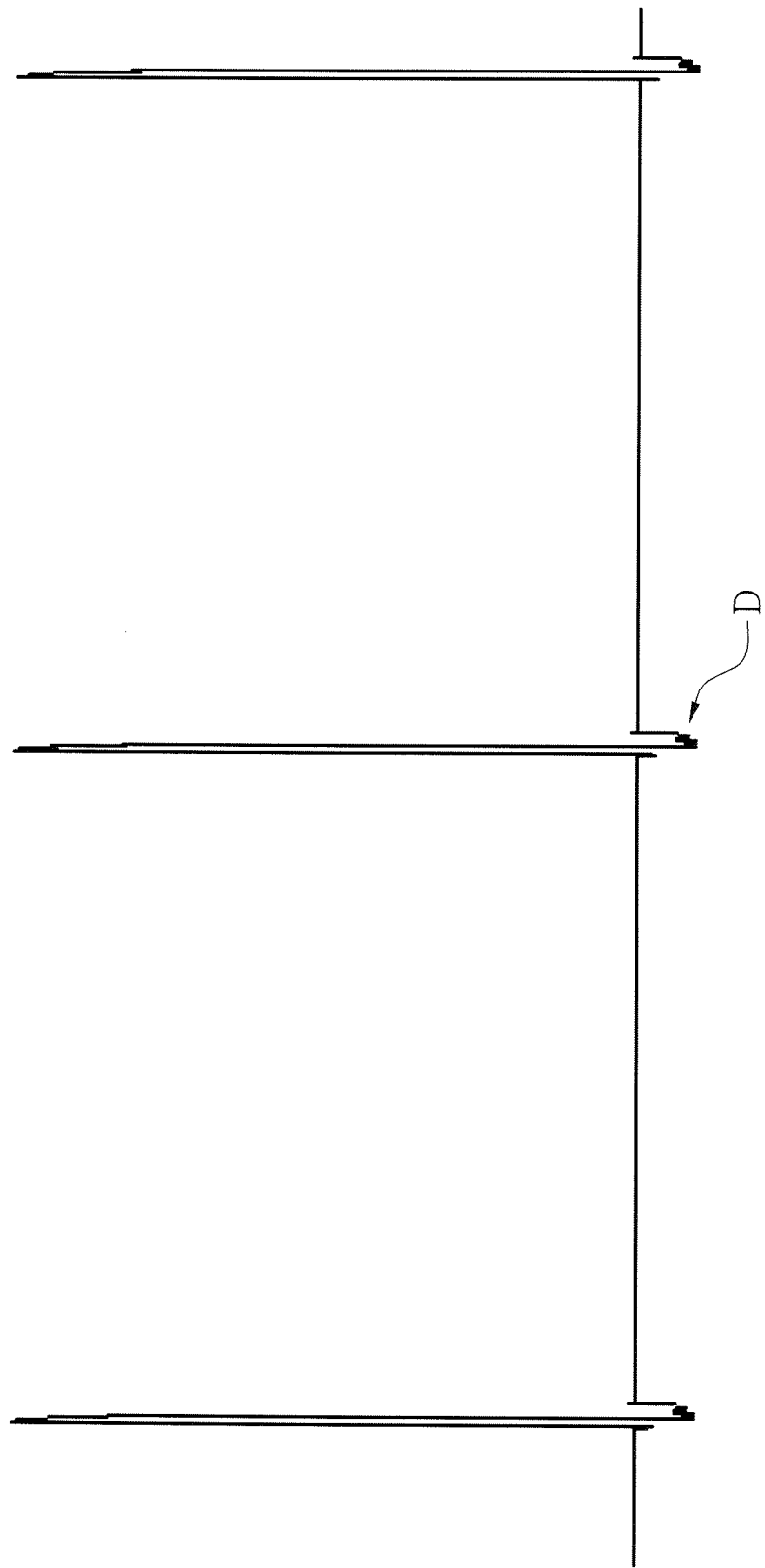
FIG. 10 illustrates a wave without being processed by the negative half-wave elimination circuit, where the wave obviously has a negative half wave.
Figure 11:
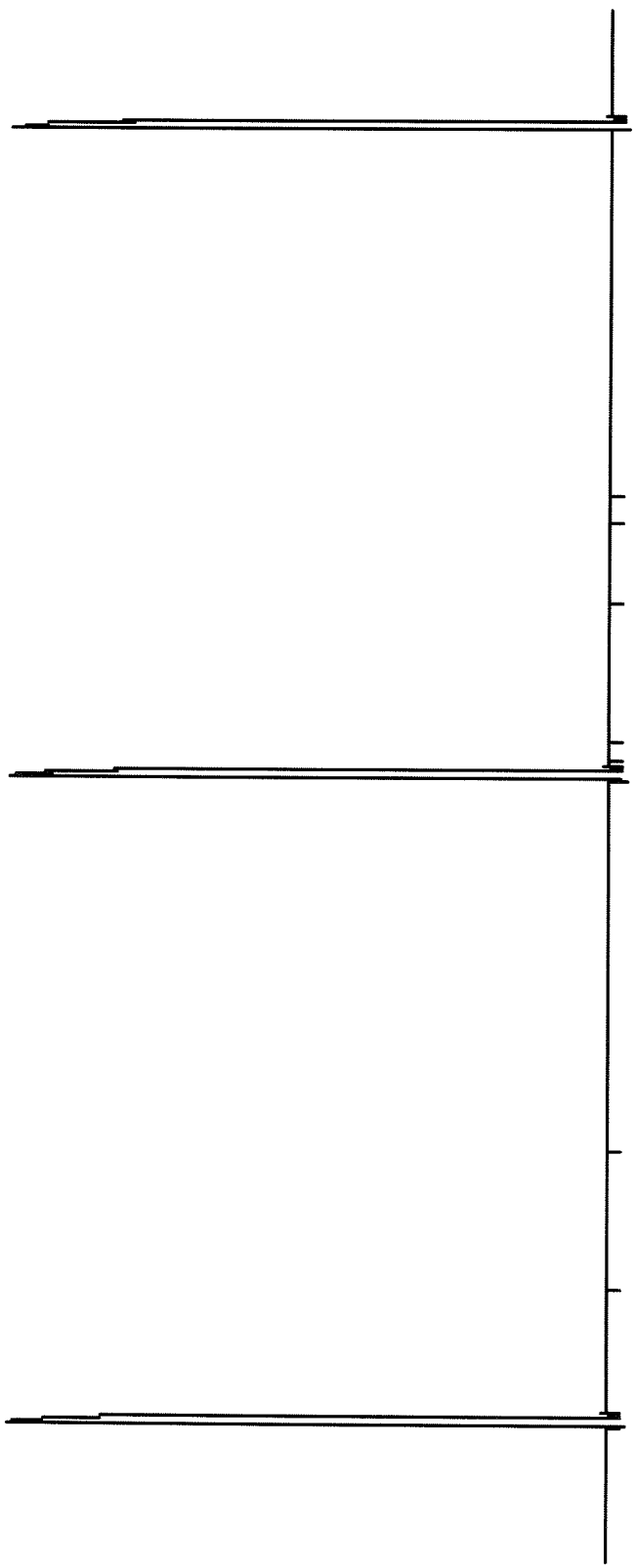
FIG. 11 illustrates a wave processed by the negative half-wave elimination circuit, where the wave does not have the negative half wave shown in FIG. 10.
Figure 12:
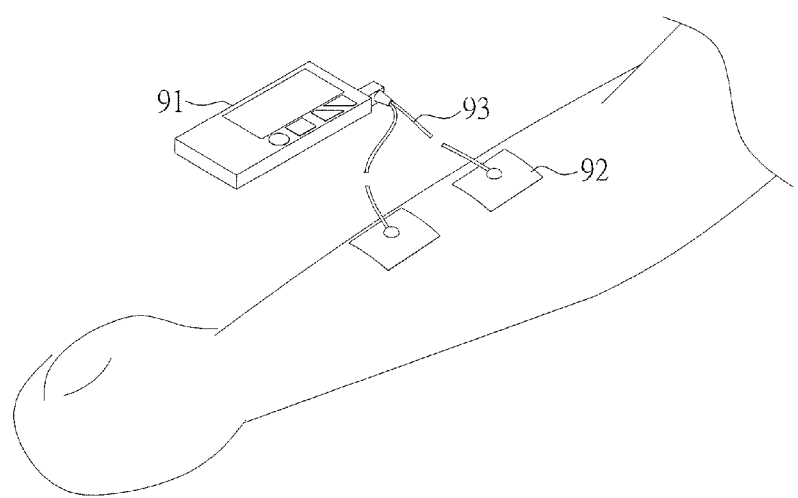
FIG. 12 illustrates a status diagram of using a conventional massager.

In the present disclosure, while the aforesaid current is passed through the treatment site of the body, the negative half cycle wave generated by the DC power supply is eliminated. In contrast, as shown in FIG. 10, in prior art the negative half wave D of the applied wave may give the body an uncomfortable tingling during the discharging treatment, and it is the reason why the conventional massager only supplies the low voltage of 0.3 to 20 volts and the low current. In the present disclosure, by arranging the negative half-wave elimination circuit 24 to generate a positive half cycle wave with a peak time of about 0.2 millisecond, the negative half cycle wave generated by the DC power supply may be eliminated. As shown in FIG. 11, it illustrates a negative half cycle wave eliminated. During the treatment, the control wave is continuously generated according to the above cycle while the DC power supply supplies the power. Thus, the uncomfortable tingling may be prevented during the aforesaid discharging treatment, and the voltage applied in the present disclosure may be up to the range from 30 to 80 volts and the current may be up to 80 mA at most, so as to achieve the effect of transmitting the current and the heat energy to the deep treatment site of the body.

Besides, the purpose of arranging the aforesaid optical coupler 27 for the user's reset is described as below. In the process of using the treatment device, if a sudden power failure or a broken circuit between the host 1 and the cushions 3 is occurred to invalid the cushions 3, the optical coupler 27 may transmit a feedback signal to the processor 22 to reset the voltage to a minimum value. Thus, if the prior setting of the voltage has a higher value, the problem of feeling the uncomfortable tingling on the treatment site may be prevented because the treatment device may not output a large voltage initially.

Therefore, by using the treatment device of the present disclosure, the cushions 3 can be pasted to the specific site of the body, to transmit the heat energy generated by the electric heating layer 32 to the deep of the treatment site. Unlike the conventional massager which may only irritate the surface skin and the shallow muscle, the heat and the low-frequency treatment device of the present disclosure may irritate the deep muscle, so as to improve the blood circulation and achieve the effect of the blood circulation. And, there will not be the illness generated by the irritation in the treatment process.

The above-mentioned descriptions represent merely the exemplary embodiment of the present disclosure, without any intention to limit the scope of the present disclosure thereto. Various equivalent changes, alternations or modifications based on the claims of present disclosure are all consequently viewed as being embraced by the scope of the present disclosure.

The invention claimed is:
1. A heat and low-frequency treatment device, comprising a host having a DC power supply, a control circuit disposed on the host and electrically connected to the DC power supply, wherein the control circuit comprises an input interface, a processor, an amplifying circuit and a negative half-wave elimination circuit, the input interface comprises a switch and an encoder, the processor provides a control signal according to an operation on the input interface, the DC power supply is electrically connected to two output electrodes through the negative half-wave elimination circuit and the amplifying circuit, one of the two output electrodes is a positive electrode and the other is a negative electrode, when the two output electrodes are conducted to each other, the voltage between the two output electrodes are in a range from 30 to 80 volts with 50 to 60 hertz correspondingly, and a conductive current is adjustable to be less than or equal to 80 mA, the negative half-wave elimination circuit is connected to the processor and the amplifying circuit correspondingly, and configured to receive the control signal and generate a positive half cycle wave with a peak time of about 0.2 millisecond according to the control signal, and use a diode to eliminate a negative half cycle wave generated by the DC power supply, and a control wave is continuously generated according to the above cycle while the DC power supply supplies the power; and
two cushions disposed on opposite sides of a treatment site of a body, wherein each of the two cushions comprises an electrode layer configured to be pasted to the treatment site and an electric heating layer configured to cover the electrode layer, the electric heating layer is electrically connected with the processor for power control, each of the electrode layer is made of a conductive material, the electrode layers of the two cushions are electrically connected to the two output electrodes correspondingly, when the processor controls the DC power supply to supply the power, the current according to the aforesaid control wave and the voltage is passed through the treatment site from the cushion connected with the positive electrode to the cushion connected with the negative electrode, and the heat energy generated by the electric heating layer is transmitted to the deep of the treatment site.

2. The heat and low-frequency treatment device according to claim 1, wherein the negative half-wave elimination circuit comprise an optical coupler with an open-circuit detection function, the optical coupler comprises a detection circuit and a light emitting diode, the light emitting diode produces light while being conducted by the DC power supply, the detection circuit generates no signal while the light emitting diode produces light, and it transmits a feedback signal to the processor while the light emitting diode does not produce light, so as to reset the voltage to a minimum value for the user's another setting.

3. The heat and low-frequency treatment device according to claim 1, wherein each of the two cushions comprise a compartment layer disposed between the electrode layer and the electric heating layer, and a soft layer disposed on the side thereof facing the electrode layer and configured to be contacted to the treatment site.

4. The heat and low-frequency treatment device according to claim 1, wherein the negative half-wave elimination circuit is connected to a half-bridge circuit to be a switch of outputting the current.

5. The heat and low-frequency treatment device according to claim 1, wherein the host comprises a monitor configured to display operation information and a buzzer configured to generate a warning sound.

6. The heat and low-frequency treatment device according to claim 1, wherein the input interface is a remote controller.

* * * * *